United States Patent [19]

Mayer et al.

[11] 4,207,270
[45] Jun. 10, 1980

[54] PHOSPHITES OF POLYALCOHOLS

[75] Inventors: Norbert Mayer, Gablingen; Gerhard Pfahler, Augsburg; Hartmut Wiezer, Gersthofen, all of Fed. Rep. of Germany

[73] Assignee: Oechst Aktiengesellschaft, Fed. Rep. of Germany

[21] Appl. No.: 908,289

[22] Filed: May 22, 1978

[30] Foreign Application Priority Data

May 25, 1977 [DE] Fed. Rep. of Germany ....... 2723526

[51] Int. Cl.$^2$ .......................... C07F 9/141; C07F 9/15
[52] U.S. Cl. ................................. 260/927 R; 260/928; 260/982; 260/953; 260/45.8 R; 252/400 R
[58] Field of Search ................... 260/927 R, 928, 953

[56] References Cited

U.S. PATENT DOCUMENTS

| 3,328,492 | 6/1967 | Gleason et al. | 260/928 X |
| 4,086,302 | 4/1978 | Morgan et al. | 260/928 X |

FOREIGN PATENT DOCUMENTS 2325648 12/1974 Fed. Rep. of Germany ........... 260/928

Primary Examiner—Anton H. Sutto
Attorney, Agent, or Firm—Connolly and Hutz

[57] ABSTRACT

The invention relates to mixed esters of phosphorous or phosphoric acid having on the one hand open chain polyalcohols and on the other hand long chain alkyl compounds with activated hydrogen, for example, alcohols, mercaptans and amines. The compounds are suitable as light and heat stabilizers for polyolefins and for chlorine-containing thermoplastic compositions and are furthermore distinguished by a high resistance to hydrolysis.

1 Claim, No Drawings

PHOSPHITES OF POLYALCOHOLS

The present invention relates to phosphites of polyalcohols, their manufacture and their use.

It is known that during the processing of synthetic polymers organic phosphites are added as co-stabilizers in addition to other stabilizers. Most of the phosphite esters used for this purpose are liquids, for example, tris-nonyl-phenyl phosphite, triphenyl phosphite or diphenyl-isooctyl phosphite. Since the other plastics stabilizers are generally solids, liquid phosphite esters, when added to the plastics powders, require special complicated dosage installation. In many cases, the liquid additives impair the mechanical properties of plastics materials. For example, if commercial liquid phosphites are added to rigid PVC, the so-called "Vicat-value", i.e. the temperature at which the plastics material begins to soften, is reduced in undesired manner. With polyolefins, the addition of liquid phosphites may lead to stress cracking corrosion which is equally undesired.

These problems have been known for a long time; it is, therefore, not surprising that solid phosphites have been proposed as stabilizers in the literature, for example esters of long chain alcohols with the branched polyol pentaerythritol (U.S. Pat. No. 2,961,454). A commercial stabilizer of this group is distearyl-pentaery-thritol diphosphite which, however, has the great disadvantage of causing discoloration if added during processing of PVC, so that it has only gained importance as stabilizer in the processing of polyolefins.

Even phosphite esters of the heterocyclic polyol anhydro-enneaheptite (U.S. Pat. No. 3,326,939) have been proposed, but have hitherto not been used in practice, probably also due to the fact that anhydro-enneaheptide, contrary to pentaerythritol or unbranched, open chain polyols, is no commercial substance so far.

Russion patent specification No. 363,707 discloses as antioxidants for the thermal stabilization of lubricating and transformer oil reaction products of hexites with triphenylphosphite of the formula

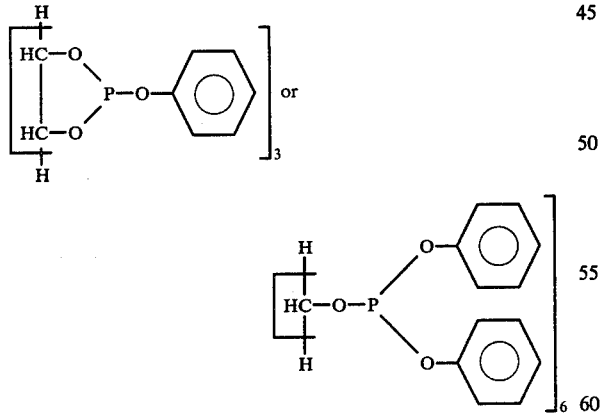

However, nothing is known about their efficiency as antioxidants in plastics materials. Furthermore these substances are oily liquids and have the above mentioned disdisadvantages. Finally they have a high susceptibility to hydrolysis which is typical for phenyl phosphites. Phenol which is liberated during hydrolysis has toxicological properties and, consequently, the use of these compounds is not advisable, both for reasons of industrial hygienics in the processing of plastics and for physiological reasons, for example when using the plastics material in the food packaging industry.

The previously proposed solid phosphites generally have a further unfavorably property of organic phosphites, which is also latent with liquid phosphites, i.e. their great susceptibility to hydrolysis. This susceptibility is not so important with the liquid phosphites, since they have naturally a small specific surface area and are generally stored in closed vessels which prevent access of atmospheric humidity. The solid phosphites, on the other hand, are marketed in the form of flowable powders or flakes for reasons of better dosage. The large specific surface area of the fine-grained phosphites considerably facilitates the attack of the onmi-present atmospheric humidity. In addition, the material from which the bags are made, which are used for the packaging of the solid phosphite stabilizers, are much more pervious to atmospheric moisture than containers for liquids. It is, therefore, understandable that the activity of usual solid phosphite stabilizers is reduced due to hydrolysis during prolonged storage.

It was, consequently, an object of the present invention to develop solid phosphite stabilizers for synthetic plastics which are especially stable to hydrolysis.

It has now been found surprisingly that this object is excellently achieved when using mixed esters of phosphorus-containing acids, unbranched, open chain polyalcohols and long chain alkyl compounds which contain a functional group with an activated hydrogen atom.

The present invention, consequently, provides compounds of the formal structure

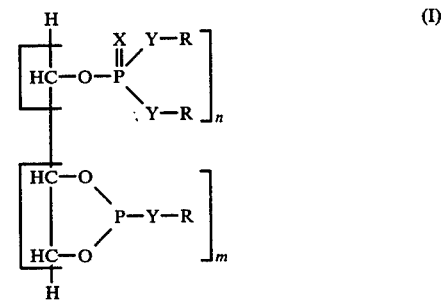

in which
n is 1, 2, 3, 4, 5 or 6 and
m is 0, 1 or 2, in which case n+2m≧3, but is not greater than 6,
X is O or no substituent,
Y is —O—, —S— or —NR'— with R' being hydrogen, or $C_{1-20}$ alkyl,
R is linear alkyl having of from 12 to 30 carbon atoms and, if Y is —O—, R may be a linear β-hydroxyalkyl radical having of from 12 to 30 carbon atoms, a 3-thia-5-hydroxyalkyl radical having from 12 to about 32 carbon atoms, or a mono- or difatty acid ester of glycerol, the fatty acid having a chain length of from 12 to 30 carbon atoms.

The invention moreover relates to a process for the preparation of the esters and to the use of these esters as stabilizers for plastics.

The abovementioned term "formal structure" means that the formula only shows the gross composition but does not give any detail on the position of the phosphite ester bond on the polyalcohol molecule and on the mutual spatial arrangement of the substituents to one another.

The polyol compounds from which the compounds according to the invention derive are unbranched and have of from 3 to 6 carbon atoms and the same number of OH groups. Examples thereof are glycerol and furthermore sugar alcohols, for example erythritol, adonitol, arabitol, dulcitol and particularly xylitol, sorbitol and mannitol.

Suitable phosphorus-containing starting compounds are derivatives of phophoric acid and preferably of phosphorus acid containing easily volatile alcohol or amine substituents which can be detached by hydrolysis, for example $PCl_3$ or $POCl_3$ or preferably hexamethylphosphorus acid triamide, hexamethylphosphoric acid triamide or tri-lower-alkyl or triaryl phosphites or phosphates, for example triphenyl phosphite, tripropyl phosphite, trimethyl phosphate and especially trimethyl and triethyl phosphite.

The radicals represented in the general formula I by the grouping —Y—R are radicals of long chain alkyl compounds, which contain a functional group with an active hydrogen atom. Examples thereof are:

(a) α-β-diols of the structure R—CH(OH)—CH$_2$OH having a chain length of from 12 to 32, preferably of from 20 to 30 carbon atoms, or mixtures of these diols. They may be obtained in a high yield by hydrolysis of the epoxides of long chain α-olefins.

(b) monoalcohols R—OH having a chain length of from 12 to about 30 carbon atoms, for example fatty alcohols and wax alcohols, which may be obtained, for example, by hydrogenation of fatty and wax acids or which are present in natural and fossil waxes, or synthesis alcohols which may be obtained by oligomerization of ethylene and which are commercially available under the name "afols" (Trade Mark). Preference is given to stearyl and behenyl alcohol. Further preferred alcohol components are the 3-thia-5-hydroxyalkyl alcohols with of from 12 to about 32 carbon atoms, which may be obtained by addition of mercaptoethanol or thioglycerol to long chain epoxides, or a mono- or di-fatty acid ester of glycerol, in which case the fatty acid has a chain length of from 12 to 30 carbon atoms.

(c) aliphatic primary mercaptans having of from 12 to 30, preferably of from 12 to 20, carbon atoms, for example octadecylmercaptan or dodecylmercaptan, (d) amines of the structure

with R' being H or $C_{1-20}$-alkyl and R" being $C_{12-30}$, preferably $C_{12-20}$ alkyl, for example laurylamine, preferably stearylamine, N-methyl-stearylamine and distearylamine, The readily obtainable esters according to the invention are prepared by transesterification of the phosphorus-containing starting materials with the polyols and the substances mentioned sub (a) to (d).

For this purpose, mixtures of representatives of the compounds shown in the individual groups and mixtures of representatives of several groups may alternatively be used. The reactants are generally used in stoichiometrical amounts; however, when using R—OH components listed sub (a) and (b), these may in some cases be suitably employed in a 5 to 50%, preferably in a 5 to 15%, excess.

The reaction may be accelerated by basic compounds, for example di- and trialkylamines, for example triethylamine, triisopropanolamine, alkali metal alcoholate, alkali metal amides and preferably alkali metal hydroxide. The catalyst is added in an amount of from 0.01 to about 5%, calculated on the total weight of the reaction batch.

The reaction temperature is in the range of from 80° to 250° C., preferably of from 120° to 180° C. It is generally chosen such that the released alcohol distills off quickly enough. It is possible, of course, and in the case of high-boiling alcohols, for example phenol, even advisable, to support the splitting off of alcohol by applying a vacuum. It is generally possible to work in the presence of an inert solvent, this procedure, however, does not bring about any advantages.

A particular simple method for preparing the compounds according to the invention is carried out in the following manner: Polyol, the derivative of phosphorous or optionally of phosphoric acid carring alcohol or amine substituents which are readily detachable by hydrolysis, and the long chain alcohols, amines or mercaptans or a mixture of these substances are introduced into the reaction vessel, optionally one of the abovementioned basic catalysts is added and the alcoholitically released substituent of the phosphorous acid is distilled off.

Naturally it is also possible to carry out the process with stepwise transesterification of the starting compounds, instead of employing an "one-pot" transesterification, i.e., for example, first only the polyol and the phosphorous acid ester of an easily volatile alcohol are reacted to give the corresponding polyphosphite ester with short chain alcohol radicals and thereafter the desired compound is synthesized in a second reaction step by adding corresponding molar quantities of long chain alcohols, amines or mercaptans and distilling off the equivalent quantities of easily volatile alcohol set free. These two transesterification steps may alternatively be carried out in reverse direction without disadvantage.

The first mentioned "one-pot" process may in some cases be advantageous, when intermediary formed compound in the two-stage process is present at the reaction temperature as a highly viscous phase which is difficult to stir and to handle. The formation of a viscous phase is not observed in the single-step process. In any case, the final products obtained are filterable liquids of low viscosity in molten state, which solidify upon cooling to give wax-like solids. They may be used as stabilizers without further purification, which may be considered as a particular advantage, although this condition makes it understandable that the products obtained are not in every case chemically uniform and may contain by-products.

Another advantage of the products according to the invention, is—in addition to the fact they are readily obtainable,—their extremely high resistane to hydrolysis. This property was not foreseeable, but a high susceptibility to hydrolysis was to be expected due to the concentration of highly polar groupings in a narrow molecular range. This prejudice was moreover confirmed by the extremely high susceptibility to hydrolysis of hexite-phenyl phosphites of the state of the art.

The phosphorous-containing compounds according to the invention are moreover distinguished by the fact that they confer upon PVC compositions to which they have been added, a high stability to discoloration under thermal stress. This property is surprising and was not foreseeable.

Unbranched polyalcohols possess, in contradistinction to pentaerythritol or anhydro-enneaheptide, hydrogen atoms in $\beta$-position with regard to the oxygen substituents so that so-called $\beta$-elimination reactions with splitting off of derivatives of phosphorous or of phosphoric acid and the formation of conjugated and even cumulated double bonds were to be expected under extreme thermal stress during the processing of plastics. As it is commonly known, these highly unsaturated compounds, react with one another to give intensely brown to black colored resins. It is, consequently, extremely surprising that this expected phenomenon is not observed, on the contrary, an extraordinary high stabilization to discoloration is found when using the compounds of the invention in PVC in the so-called "furnace test", i.e. the examination of the static heat stability (furnace stability).

Moreover, with the phosphites according to the invention the processing stability of moldable plastics compositions, especially on the basis of PVC, can be greatly improved. With regard to this property, the phosphites are distinctly superior to commercial products. This effect, too, is extremely surprising with regard to the aforesaid structural and chemical reasons and could not have been foreseen.

The addition of the phosphite compounds according to the invention in the presence of metal compounds known as stabilizers, epoxide stabilizers and optionally polyhydric alcohols moreover improves the heat and light stability not only in the processing of polyvinyl chloride, but also of chlorine-containing vinyl-homo- and copolymers, for example polyvinylidene chloride, polyvinyl chloroacetate and vinyl chloride-$\alpha$-olefin-copolymers.

Metal compounds known as stabilizers in the context are calcium, barium, strontium, zinc, cadmium, magnesium, aluminum and lead soaps of aliphatic carboxylic acids or of hydroxycarboxylic acids having approximately 12 to 32 carbon atoms, or of phenol-substituted aliphatic carboxylic acids, salts of said metals with aromatic carboxylic acids, for example benzoates, salicylates and (alkyl)phenolates of these metals, organo-tin compounds, for example dialkyltin thioglycolates and carboxylates. Known epoxide stabilizers are, for example epoxidized soybean oil, tall oil, linseed oil, and epoxidized butyl oleate and the epoxides of long chain $\alpha$-olefins.

Suitable polyhydric alcohols are for example pentaerythritol, trimethylol propane, sorbitol, or mannitol, i.e. preferably alcohols having 5 or 6 carbon atoms and 3 to 6 hydroxyl groups.

A suitable stabilizer combination for the processing of halogen-containing plastic compositions consists, for example, of 0.005 to 5, preferably 0.05 to 3 and especially 0.1 to 1, part by weight of one or several phosphite compounds according to the invention, 0.1 to 10, preferably 0.5 to 5, parts by weight of metal compounds known as a stabilizer, 0.1 to 10, preferably 0.5 to 5, parts by weight of a known epoxide stabilizer and 0 to 1 part by weight of a polyhydric alcohol, calculated on 100 parts by weight of polymer.

The compounds according to the invention are also very efficient in the stabilization of polyolefins. The addition of a usual amount thereof (less than 1% by weight) to polypropylene considerably improves the stability to light and heat, especially in the presence of phenolic and optionally sulfidic antioxidants.

Phenolic and sulfidic stabilizers are intended to include the heat stabilizers generally used in plastics processing, for example 3,5-di-tert.butyl-4-hydroxyphenyl-propionic acid esters, 2,5-ditert.butyl-p-cresol, alkylidene-bis-alkylphenols, esters and salts of bis (4'-hydroxy-3'-tert.butylphenyl)-butanoic acid or of cycloalkylidene-bis(alkylphenol)carboxylic acids or thiodipropionic acid esters of fattty alcohols or dioctadecyl sulfide and disulfide.

A stabilizer combination in the processing of halogen-free poly-$\alpha$-olefins, for example high, medium and low pressure polymers of $C_2$ to $C_4$-$\alpha$-olefins, especially polyethylene and polypropylene, or of copolymers of such $\alpha$-olefins, consists for example, of 0.005 to 3, preferably of 0.01 to 1 parts by weight of a phenolic stabilizer, 0.01 to 2, preferably 0.05 to 0.5, parts by weight of the calcium salt of a fatty acid or a wax acid optionally 0.005, preferably 0.01 to 1, part by weight of a sulfidic stabilizuer and 0.005 to 5, preferably 0.05 to 1, part by weight of one or several compounds of the invention, for 100 parts by weight of polymer. If necessary, 0.01 to 3 parts by weight of a special UV stabilizer can be added to the mixture. From among the great number of commercial UV stabilizers the following are named by way of example: alkoxyhydroxy-benzophenones, hydroxyphenyl-benzotriazoles, salicylic acid phenol esters, benzoic acid hydroxyphenol esters, benzylidenemalonic acid nitrile esters and so-called "quenchers" such as nickel chelates, hexamethyl-phosphoric acid triamide or piperidine stabilizers known as hindered amine light stabilizers (HALS proucts).

Mixtures of the compounds according to the invention with known stabilizers improve the stability not only of polyolefins and of chlorine-containing polymers, but also of polyesters, polyamides, phenol-formaldehyde resins, epoxide resins, polystyrene, polyacrylonitrile, polycarbonate, polysiloxanes, polyethers, polyurethanes and SBR rubber mixtures.

The following examples illustrate the invention:

EXAMPLE 1

Dodeca-stearyl-sorbityl-hexaphosphite

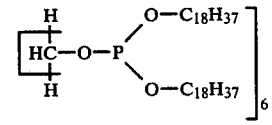

A mixture of
18.2 g (0.1 mol) of sorbitol,
104 g (108 ml; 0.63 mol) of triethyl phosphite,
324 g (1.2 mols) of stearyl alcohol and
1 drop of triethylamine
which is placed in a 500 ml three-necked flask provided with a stirrer, a gas inlet, a 10 cm Vigreux column and a distillation bridge is stirred at a bath temperature of about 120° C., while dry nitrogen is passed through. After about 1 hour, ethanol begins to distill off. The bath temerature is then regulated in a manner such that the outlet temperature of the distillation bridge does not exceed the boiling temperature of ethanol (78° C.). About 88 ml of ethanol distill over. Near the end of the reaction, the bath temperature is increased to about 200° C.

When the ethanol development is terminated, water jet vacuum is applied for a short time in order to remove triethyl phosphite which has not been converted. The molten product is then filtered through a heated folded filter and subsequently allowed to cool. There is obtained a substance which melts at a temperature of from 42.5° to 43° C. According to thin layer chromatography, the prouct is free from substantial quantities of tristearyl phosphite.

EXAMPLES 2 to 4

According to the procedure of Example 1, the compounds shown hereunder are prepared by reacting xylitol, erythritol and glycerol respectively on the one hand with each time 1 mol of triethyl phosphite and on the other hand with each time 2 mols of stearyl alcohol:

deca-stearyl-xylityl-pentaphospite of melting point 41° C.

octa-stearyl-erythrityl-tetraphosphite of melting point 45° to 50° C.

hexa-stearyl-glycerinyl-triphosphite of melting point 48° to 50° C.

According to thin layer chromatographic analysis, these substances are also free from substantial quantities of tristearyl phosphite.

EXAMPLE 5

Undeca-stearyl-mono-(α-hydroxy-triacontyl)-sorbityl-hexaphosphite

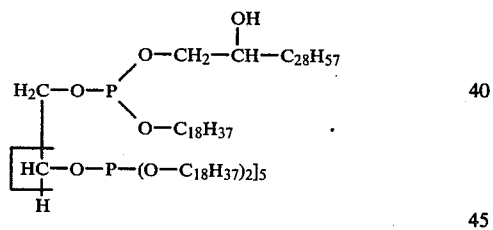

The substance is prepared analogously to Example 1 by transesterification of 6 mols of triethyl phosphite with 1 mol of sorbitol, 11 mols of stearyl alcohol and 1 mole of 1,2-dihydroxy-triacontan (which has been obtained by hydrolysis of the $C_{30}$ epoxide disclosed in Examples 9 to 12 of German Auslegeschrift No. 2,436,817). The product melts at a temperature of from about 55° to 59° C.

EXAMPLE 6

Hexa-stearyl-hexa-stearylamino-sorbityl-hexaphosphite

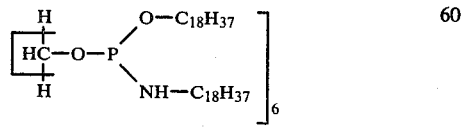

The substance is prepared analogously to Example 1 by reacting 1 mol of sorbitol and 6 mols of stearyl alcohol, stearylamine and triethyl phosphite respectively.

The melting point is in the range of from about 58° to 60° C.

EXAMPLE 7

Nona-stearyl-sorbityl-pentaphosphite

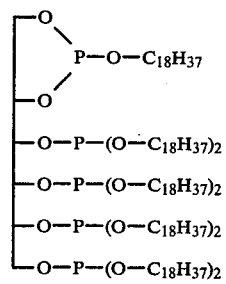

This compound is prepared according to the procedure of Example 1 by reacting 9 mols of stearyl alcohol, 1 mol of sorbitol and 5 mols of triethyl phosphite. The product has a melting point of 49° C.

EXAMPLE 8

Hexa-stearyl-sorbityl-tetraphosphite

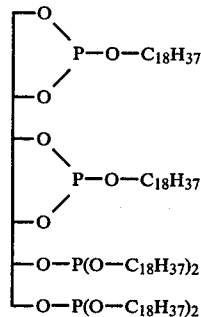

This compound is prepared by reacting 6 mols of stearyl alcohol, 1 mol of sorbitol and 4 mols of triethylphosphite according to the procedure of Example 1. The melting point is at 52° C.

EXAMPLE 9

Penta-stearyl-(α-hydroxytriacontyl)-sorbityl-tetraphosphite

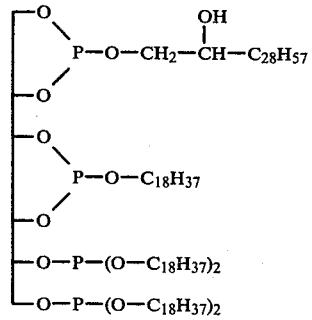

The compound is prepared by reacting 1 mol of sorbitol with 1 mol of 1,2-dihydroxytriacontan, 5 mols of stearyl alcohol and 4 mols of triethylphosphite analogously to Example 1. The melting point is in the range of from 75° to 76° C.

EXAMPLE 10

Penta-stearyl-thiostearyl-sorbityl-tetraphosphite

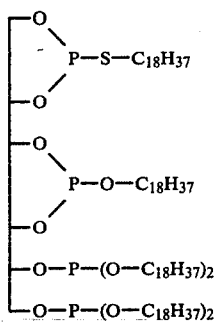

The compound is prepared by reacting 1 mol of sorbitol, 1 mol of stearylmercaptan, 4 mols of triethylphosphite and 5 mols of stearyl alcohol analogously to Example 1. The product melts at a temperature of from 45° to 46° C.

EXAMPLE 11

Penta-stearyl-(3-thia-5-hydroxy-tritriacontyl)-sorbityl-tetraphosphite

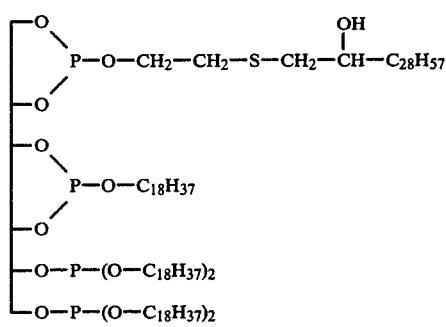

The product is prepared from 1 mol of sorbitol, 1 mol of 1,5-dihydroxy-3-thia-tritriacontan (according to German Offenlegungsschrift No. 2,636,729), 5 mols of stearyl alcohol and 4 mols of triethyl phosphite in the presence of 0.5 g of KOH. The melting point is at 62.5° C.

EXAMPLE 12

Penta-stearyl-stearylamino-sorbityl-tetraphosphite

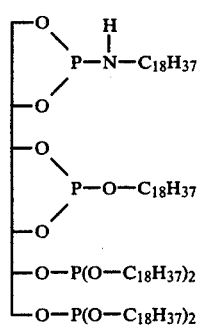

The product is obtained by reacting 1 mol of stearylamine, 5 mols of stearyl alcohol, 1 mol of sorbital and 4 mols of triethyl phosphite according to Example 1. It melts at a temperature of 51° C.

EXAMPLE 13

Hexa-stearyl-mannityl-tetraphosphite

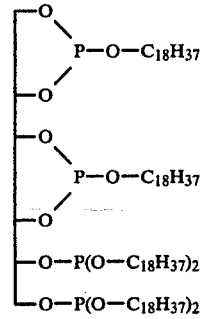

The substance is prepared by reacting 1 mol of mannitol, 4 mols of triethyl phosphite and 6 mols of stearyl alcohol. The product melts at a temperature of 47° C.

EXAMPLE 14

Tetra-stearyl-xylityl-triphosphite

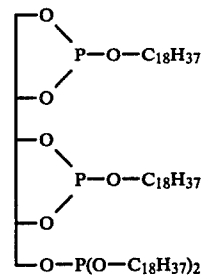

The product which may be prepared by reacting 1 mol of xylitol, 4 mols of stearyl alcohol and 3 mols of triethyl phosphite according to Example 1 has a melting point of from 47° to 47.5° C.

EXAMPLE 15

Penta-stearyl-erythrityl-triphosphite

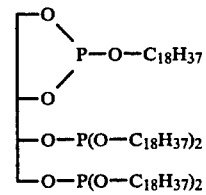

The compound is prepared by reacting 1 mol of erythritol, 5 mols of stearyl alcohol and 3 mols of triethyl phosphite. It melts at a temperature of 57° C.

EXAMPLE 16

Tri-stearyl-glycerinyl-diphosphite

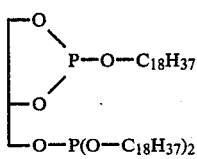

The product may be prepared by reacting 1 mol of glycerol, 2 mols of triethyl phophite and 3 mols of stearyl alcohol according to the procedure of Example 1. The product melts at a point of from 42° to 44° C.

EXAMPLE 17

Tri-stearyl-glycerinyl-monophosphite-monophosphate

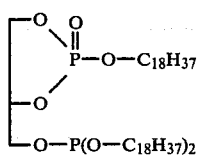

92 g (1 mol) of glycerol, 180 ml (1 mol) of triethyl phosphite, 117 ml (1 mol) of freshly distilled trimethyl phosphate, 810 g (3 mols) of stearyl alcohol and 1 g of KOH are stirred in a nitrogen current at a temperature of from 120° to 200° C., until no more alcohol distills over a 20 cm Vigreux column. The residue in the hot state is filtered through a steam-heatable folded filter. A colorless product melting at 42° C. is obtained.

EXAMPLE 18

This example is intended to show the surprisingly high stability to hydrolysis of the phosphites according to the invention, which is examined in the following manner:

5 g each of the respective phosphite are boiled for 20 and 60 minutes in 100 ml of deionized water. The mixture is then allowed to cool, the aqueous phase is filtered off through a folded filter and in the filtrate the phosphorous or phosphoric acid set free is titrated with 0.1 N KON against bromophenol blue.

In the following table is indicated the degree of hydrolysis determined under specific conditions, as quotient of the actual consumption of KOH and the theoretically possible consumption of KOH with a complete hydrolysis. For comparative purposes, the stability to hydrolysis of other phosphites known as stabilizers was determined.

| phosphite of Example | (in % of theory) degree of hydrolysis after | |
|---|---|---|
| | 20 minutes | 60 minutes |
| 1 | 26 | 42 |
| 5 | 30 | 51 |
| 7 | 29 | 43 |
| 9 | 37 | 49 |
| 13 | 41 | 52 |
| 17 | 49 | 51 | comparative phosphites:

| phosphite of Example | (in % of theory) degree of hydrolysis after | |
|---|---|---|
| | 20 minutes | 60 minutes |
| distearyl-pentaerythrityl-diphosphite | 55 | 68 |
| triphenyl phosphite | 84 | 100 |
| trisnonylphenyl phosphite | 57 | 92 |
| di-phenyl-isooctyl-phosphite | 55 | 72 |
| dodeca-phenl-sorbityl-hexaphosphite | 89 | — |
| triphenyl-sorbityl-triphosphite | 70 | — |

The low stability to hydrolysis of the sorbityl phenylphosphites according to Russian patent specification No. 363,707 is remarkable in the contexte.

EXAMPLE 19

This example is intended to demonstrate the utilitarian properties of the phosphites of the invention is polyvinyl chloride. The parts in the following description are parts by weight.

Each time 100 parts of a mass polyvinyl chloride having a K value of 60 are intimately mixed with
- 0.2 part of 2-phenyl-indole,
- 3.0 parts of epoxidized soybean oil
- 0.25 part of a complex calcium/zinc stabilizer consisting of 42% by weight of calcium stearate, 30% by weight of zinc stearate, 22% by weight of pentaerythritol and 6% by weight of 2,6-di-tert.butyl-4-methylphenol
- 0.2 part of a montanic acid ester (acid number 18, saponification number 154
- 0.3 part of stearyl stearate
- 0.5 part of glycerol monostearate and
- 0.5 part of the respective phosphite of the invention.

To measure the dynamic heat stability (rolling stability) the mixtures are rolled on a two roll mill at 180° C. and with 20 revolutions per minute. At intervals of 10 minutes samples are taken from the rough sheet and the color of the samples is compared with the colors of a proper color shart. Rolling is continued until the rough sheet has turned black.

In order to measure the static heat stability (furnace stability) a rough sheet is prepared as described above and the sheet is rolled for a further 10 minutes at 180° C. Samples having a diameter of about 30 mm are punched out of the rough sheet removed from the mill and having a thickness of about 0.5 mm, the samples are wrapped in aluminum foil and heated to 180° C. in a heating cabinet with air circulation. At intervals of 10 minutes a sample is taken from the cabinet. In the following table the time is indicated until the sample has turned black.

In the color chart used the individual notes have the following meaning:
- 1=water clear
- 2=slightly yellowish
- 3=intense yellow color
- 4=dark yellow-brown color
- 5=dark brown to black It can be seen from the following table that the phosphites of the invention give excellent results as regards the dynamic as well as the static stabilization effect and that they are distinctly superior to commercial phosphites.

| phosphite of Example | dynamic (heat) stability discoloration of rough sheet after rolling time of .... minutes | | | | | | | | static (furnace) stability black coloration at 180° C. after ..... minutes |
|---|---|---|---|---|---|---|---|---|---|
| | 10' | 20' | 30' | 40' | 50' | 60' | 70' | 80' | |
| 1 | 1 | 1–2 | 2 | 3–4 | 3 | 3 | 4 | 4 | 60' |
| 5 | 1 | 1 | 1–2 | 2–3 | 3 | 4 | 5 | — | 60' |
| 8 | 1 | 1–2 | 2 | 2–3 | 3 | 3 | 4 | 5 | 60' |
| 9 | 1 | 1–2 | 1–2 | 2–3 | 3 | 4 | 5 | — | 60' |
| 16 | 1–2 | 1–2 | 2 | 2–3 | 3 | 4 | 5 | — | 60' |
| 17 | 1 | 1–2 | 2 | 2–3 | 3 | 5 | — | — | 60' |
| Comparison: | | | | | | | | | |
| distearylpentaerythrityl diphosphite | 2–3 | 2–3 | 3 | 4 | 5 | — | — | — | 50' |
| triphenyl phosphite | 1 | 2 | 2–3 | 5 | — | — | — | — | 50' |
| trisnonylphenyl phosphite | 1 | 2 | 2–3 | 3 | 5 | — | — | — | 40' |
| diphenyl-isooctyl-phosphite | 1 | 2–3 | 3 | 5 | — | — | — | — | 70' |

EXAMPLE 20

This example is intended to demonstrate the stabilizing effect of the phosphites of the invention in polypropylene.

A mixture of 100 parts of unstabilized pulverulent polypropylene having a density of 0.90 (melt index is about 6 g/10 min, determined analogous to ASTM D 1238-62 T)

0.15 part of laurin-thiodipropionic acid ester 0.10 part of 3,3-bis-3'-tert.butyl-(4'-hydroxy-phenyl)-butanoic acid ester, 0.20 part of calcium stearate and 0.30 part of a phosphite of the invention is homogenized for 5 minutes at 200° C. on a two roll mill. The molten plastics composition is then molded at 200° C. into a sheet 1 mm thick and from the cold sheet test specimens according to DIN 53,455 are cut out.

To determine the stability to light the test specimens are exposed to the changing light of a Xenotest apparatus, (Trade Mark) type 150, by Messrs. Hanau Quarzlampen GMBH, the irradiation intensity being modulated by 6IR filters and 1 UV window (DIN 53,387). The time of exposure in hours is measured after which the absolute elongation at break has dropped to 10% of the initial value. The elongation at break is measured in the Instron tensile testing machine at a draw off speed of 5 cm/min. The energy of radiation absorbed per square centimeter is calculated from the time of exposure and the intensity of irradiation.

The test results are listed in the following table.

| phosphite of Example | exposure time in hours | radiation energy (KJ/cm$^2$) |
|---|---|---|
| 1 | 546 | 11.9 |
| 7 | 665 | 14.5 |
| 9 | 634 | 13.8 |
| without | 195 | 4.7 |

It can be seen that the phosphites of the invention are excellently suitable for stabilizing polyolefins.

We claim:

1. Compounds of the general formula I

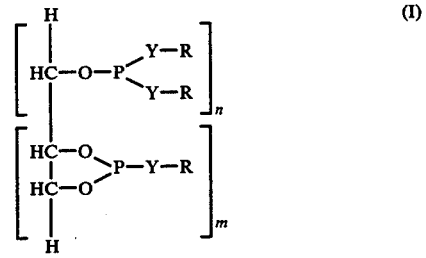

in which n is 1, 2, 3, 4, 5, or 6 and m is 0, 1 or 2, in which case n+2m=3, but is not greater than 6, Y is —O—, —S— or —NR'— with R' being hydrogen, or $C_{1-20}$ alkyl, R is linear alkyl having of from 12 to 30 carbon atoms and, if Y is —O—, R may be a linear β-hydroalkyl radical having of from 12 to 30 carbon atoms, or a 3-thia-5-hydroxyalkyl radical having from 12 to about 32 carbon atoms.

* * * * *

UNITED STATES PATENT AND TRADEMARK OFFICE
CERTIFICATE OF CORRECTION

PATENT NO. : 4,207,270
DATED : June 10, 1980
INVENTOR(S) : Norbert Mayer et al

It is certified that error appears in the above-identified patent and that said Letters Patent are hereby corrected as shown below:

Front page, left hand column, item [73] change "Oechst" to -- Hoechst --.

Signed and Sealed this

Ninth Day of December 1980

[SEAL]

Attest:

SIDNEY A. DIAMOND

Attesting Officer

Commissioner of Patents and Trademarks